United States Patent [19]

Liauw et al.

[11] 4,282,165

[45] Aug. 4, 1981

[54] PREPARATION OF TRIMETHYLTIN CHLORIDE FROM DIMETHYLTIN DICHLORIDE

[75] Inventors: Koei-Liang Liauw, Wyckoff; Michael H. Fisch, Wayne, both of N.J.

[73] Assignee: Argus Chemical Corporation, Brooklyn, N.Y.

[21] Appl. No.: 133,041

[22] Filed: Mar. 24, 1980

[51] Int. Cl.[3] .......... C07F 7/22

[52] U.S. Cl. .......... 260/429.7

[58] Field of Search .......... 260/429.7

[56] References Cited

U.S. PATENT DOCUMENTS

| | | | |
|---|---|---|---|
| 3,519,665 | 7/1970 | Molt et al. | 260/429.7 |
| 3,857,868 | 12/1974 | Witman et al. | 260/429.7 |
| 3,901,824 | 8/1975 | Knezevic et al. | 260/429.7 X |

OTHER PUBLICATIONS

Sisido et al., J. Organometallic Chem. 9, 99–107, 109–115, (1967).

Sisido et al., J. Organometallic Chem. 11, 503–513, (1968).

*Primary Examiner*—Helen M. S. Sneed

*Attorney, Agent, or Firm*—Albert L. Gazzola; Morton Friedman

[57] ABSTRACT

A trialkyltin chloride in which the alkyl groups have from about one to six carbon atoms is prepared, without detectable tetraalkyltin, from the corresponding dialkyltin dichloride in one step and in high yield using a catalyst mixture comprising a trihydrocarbylamine or trihydrocarbylphosphine and stannic chloride.

10 Claims, No Drawings

PREPARATION OF TRIMETHYLTIN CHLORIDE FROM DIMETHYLTIN DICHLORIDE

FIELD OF THE INVENTION

This invention relates to an improved method for the preparation of useful organotin compounds. More specifically, this invention relates to the preparation of relatively pure trialkyltin halides, in which there are three alkyl groups linked to tin through carbon. These products have generally far greater useful biological activity than organotin compounds which have one or two alkyl groups linked to tin through carbon. Tetraalkyltin compounds which have "four alkyl" groups linked to them, are devoid of useful biological activity and exhibit considerable mammalian toxicity, believed to result from conversion of tetraalkyltin to trialkyltin compound within the living organism.

Trialkyltin compounds exhibiting useful biological activity include, for example, the trimethyltin sulfinate compound insecticides disclosed by R. J. Strunk in U.S. Pat. No. 4,089,972 of May 16, 1978, tricyclohexyltin dithiophosphonic amide compound insecticides disclosed by D. R. Baker in U.S. Pat. No. 3,947,161 of Mar. 3, 1976 and tri-n-hexyltin organosulfonyl methane compound insecticides disclosed by D. Peterson in U.S. Pat. No. 3,850,970 of Nov. 26, 1974; tri-n-butyltin fluoride used to combat the growth of barnacles, mollusks, and tubeworms in marine environments; and tri-n-butyltin oxide used to combat the growth of mildew in paint films and bacteria in hospital environments.

In the production of each of these and other biologically useful trialkyltin compounds, a trialkyltin chloride is used as the key intermediate to introduce the trialkyltin group into the desired compound. A need therefore exists for a method for producing trialkyltin chlorides economically and safely in terms of minimizing the formation of toxic side products and exposure to these compounds and by-products by people involved in their manufacture.

PRIOR ART

Trialkyltin chlorides having long been known and many methods of preparation have been disclosed. Probably the most versatile method applicable to the preparation of many trialkyltin chlorides in at least fair yields is the scrambling or exchange reaction of a tetraalkyltin with stannic chloride, whereby the tetraalkyltin reactant functions as a source of alkyl radicals transferred to stannic chloride, resulting in a product mixture containing one or more dealkylation products of tetraalkyltin and one or more alkylation products of stannic chloride; the exact nature and proportions of these products depends on the reaction conditions, i.e., temperature and the relative proportions of the reactants. Thus tetra-n-butyltin and stannic chloride for instance, by the application of various reactants, ratios and temperatures, are known to produce the following products:

1. Mixture of approximately equal amount of tri-n-butyltin chloride and monobutyltin trichloride (British Pat. No. 739,883 of Nov. 2, 1955).
2. Mixture of di-n-butyltin dichloride and monobutyltin trichloride, with minor amounts of tri-n-butyltin chloride. (French Pat. No. 1,318,310 of Jan. 7, 1963).
3. Mixture of predominantly dibutyltin dichloride with minor amounts of tributyltin chloride and monobutyltin trichloride. (G. van der Kerk et al, J. Appl. Chem. 195, Vol. 4, p. 301 (1954).
4. Mixture of predominantly tri-n-butyltin chloride with minor contaminant amounts of tetrabutyltin and dibutyltin dichloride (G. van der Kerk et al, ibid. 1957, Vol. 6, p. 95).

Furthermore, conditions that favor the formation of a particular product of the scrambling reaction vary greatly with the nature of the alkyl group linked to tin. E. van den Berghe et al (J. Organometallic Chem. 1966. vol. 6 pp. 522–527) show that the interaction of stannic chloride with tetramethyltin, formation of dimethyltin dichloride is observed at temperatures as low as −10° C., while in the 90°–120° C. range the concentrations of methyltin trichloride, dimethyltin dichloride, and trimethyltin chloride present in a reaction mixture change rapidly, with the first compound disappearing entirely, the second reaching a maximum, and trimethyltin chloride reaching a minimum concentration.

In contrast to van den Berghe's report, P. Kushlefsky in U.S. Pat. No. 3,389,158 of June 18, 1968 show a process for preparing trimethyltin halide by reacting 3 equivalents of tetramethyltin with one equivalent of stannic halide at temperatures above the melting point of tetramethyltin and below 100° C.

It is seen from the foregoing that the literature provides conflicting reports on the production of trialkyltin halides by the scrambling reaction of tin tetrahalide with a tetraalkyltin. However, even when favorable conditions can be defined there remains the serious hazard of the tetraalkyltin, i.e., its volatility, flammability, and high toxicity.

Formation of trialkyltin halides by the chemical interaction of a stannic tetrahalide with an alkylating agent such as an alkyl compound of a metal such as magnesium, alkali metal, aluminum, or lead is also known. However, by these methods, often the formation of tetraalkyltin predominates over the formation of trialkyltin halide. For example, A. Wowk in British Pat. No. 1,085,002 of Sept. 27, 1967 discloses a reaction of stannic chloride with trialkylaluminum in the presence of alkali metal halide to complex and render harmless the by-product aluminum chloride, which results in products containing 65 to 85% tetraalkyltin and 15 to 35% trialkyltin halide. J. Natoli in U.S. Pat. No. 3,432,531 of Mar. 11, 1969 described a modified Grignard agent (alkylmagnesium halide) reaction with stannic chloride, which furnishes trialkyltin chloride and tetraalkyltin in proportions ranging from about 3:1 to about 1:5 by weight. E. Bulten in U.S. Pat. No. 3,754,012 of Aug. 21, 1973 shows reactions of stannic chloride with tetramethyllead that proceed by the following scheme:

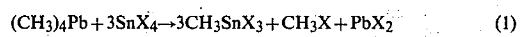

$$(CH_3)_4Pb + 3SnX_4 \rightarrow 3CH_3SnX_3 + CH_3X + PbX_2 \quad (1)$$

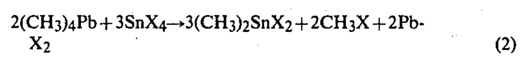

$$2(CH_3)_4Pb + 3SnX_4 \rightarrow 3(CH_3)_2SnX_2 + 2CH_3X + 2PbX_2 \quad (2)$$

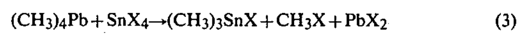

$$(CH_3)_4Pb + SnX_4 \rightarrow (CH_3)_3SnX + CH_3X + PbX_2 \quad (3)$$

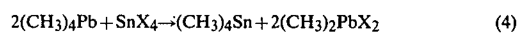

$$2(CH_3)_4Pb + SnX_4 \rightarrow (CH_3)_4Sn + 2(CH_3)_2PbX_2 \quad (4)$$

The foregoing reactions, just like the scrambling reaction, involve the handling of a tetraalkylated metal compound and its attendant hazards as either a co-product or a starting material.

Another well-known method for producing alkyltin compounds involves the alkylation of metallic tin with an alkyl halide, usually in the presence of an activating metal having a greater electrode potential than tin and/or a catalyst. Alkyltin compound products of such reactions usually include trialkyltin chlorides in minor amounts, at best, of mixtures.

For instance, S. Blitzer et al. in U.S. Pat. No. 2,852,543 of Sept. 6, 1958, prepare a mixture of organotins by alkylating a sodium-tin alloy with alkyl chloride under pressure at 160°-200° C.; the tin conversion is from 18-35%. T. Yatagi et al. in U.S. Pat. No. 3,085,102 of Apr. 9, 1963 alkylate tin with an alkyl halide in the presence of an iodide, a metal other than tin, and an inert oxygen containing solvent; they obtain mixtures of alkyltin halides. Nitto Chemical's British Pat. No. 1,053,996 of Jan. 4, 1967, teaches the alkylation of tin with alkyl halide in the presence of nitrogen or phosphorous catalyst with iodine or an iodide. The examples of Nitto show the presence of trialkyltin chlorides in the products in amounts ranging from about 2% to about 13% of the total amount of alkyltin product obtained.

In P. Hoye's U.S. Pat. No. 3,415,857 of Dec. 10, 1968 is disclosed, for the direct alkylation of tin with an alkyl halide, a catalyst system consisting of an onium compound, i.e. an organic quaternary ammonium or phosphonium halide, with a preformed stannous halide or an organotin halide in substantially equimolar proportions to the onium compound, and optionally a metal other than tin. The onium compound may be formed in situ, or added preformed. The recycle of the catalyst residue is also demonstrated. When recycling it is suggested to interrupt distilling off the organotin halides before completion, thus eliminating the need for adding organotin halide or stannous halide to the onium compound in a batch or continuous process. As a matter of fact, dialkyltin dichlorides are only obtained in reasonable yields by recycling the catalyst, as exemplified by Examples 10 and 11.

Molt et al., in U.S. Pat. No. 3,519,665 of July 7, 1970 disclose a process for preparing dialkyltin dichlorides by direct alkylation of tin metal with an alkyl chloride in the presence of a tetraalkylphosphonium or ammonium iodide as catalyst, and recycling all of the organotin chlorides remaining after distilling off and then recrystallizing the dialkyltin dichlorides, i.e. recombining the original catalyst with the distillate and filtrate residue of the dialkyltin dichlorides after each run. As the examples of this patent show, in the first run, i.e. before an residual organotin chlorides are returned to the onium catalyst, the tin conversions are poor and substantial amount of trialkyltin chloride are formed, except for Example 4 where preformed diorganotin dichloride is added to fresh tetraalkylphosphonium or ammonium iodide.

V. Knezevic et al in U.S. Pat. No. 3,901,824 of Aug. 26, 1975, incorporated herein by reference, disclose a new catalyst system for the production of dimethyltin dichloride from methyl chloride and tin metal, including a combination of a trihydrocarbyl phosphine or a trihydrocarbyl amine with tin tetrachloride. A feature of the Knezevic et al methylation of tin with the new catalyst is that the formation of trimethyltin chloride is largely suppressed, and dimethyltin dichloride products containing less than 0.1% trimethyltin chloride are obtained.

Additional disclosures of the alkylation of metallic tin in presence of an active metal include the process of B. Giannaccari et al in U.S. Pat. No. 3,651,108 of Mar. 31, 1972, in which a mixture of subdivided tin metal and an alkali or alkaline earth metal is alkylated with alkyl halide in the presence of an onium compound and/or Lewis base catalyst. In Giannaccari's process. the product is shown to be tetraalkyltin. Similarly, T. E. Jones in U.S. Pat. No. 4,092,340 of May 30, 1978 discloses the preparation of tetraalkyltin by the reaction of alkyl halide with tin in the presence of metallic zinc and tetraalkylammonium or tetraalkylphosphonium halide catalyst.

K. Sisido et al in J. Organometallic Chem. 1968, Vol. 11, on pp. 503-613 teaches a direct synthesis of organotin compounds by the conversion of a dialkyltin chloride to trialkyltin chloride and tetraalkyltin in the presence of a metal such as tin, iron, magnesium, aluminum, nickel, cobalt, or zinc, and a reaction medium of water, methanol, or tetrahydrofuran. Yields of trialkyltin chloride ranged from 4 to 76%, accompanied by varying amounts of unreacted dialkyltin dichloride and bis(-dialkylchlorotin)oxide formed in a side reaction.

SUMMARY OF THE INVENTION

In accordance with this invention, a trialkyltin chloride in which each alkyl group contains 1 to 6 carbon atoms, is prepared by heating a mixture containing at least one dialkyltin dichloride, a polyvalent metal, and a polar liquid, in the presence of a catalytic amount of a catalyst mixture of stannic chloride and a trihydrocarbylamine or phosphine having the formula $R_3E$ in which each R is a nitrogen or phosphorus, in molar proportions of stannic chloride to $R_3E$ ranging from about 1:4 to about 1:1.

It is indeed surprising that the catalyst composition in the present process, containing a trihydrocarbyl amine or phosphine, enhances the formation of trialkyltin chloride, in view of Knezvic et al, in U.S. Pat. No. 3,901,824, cited hereinbefore, which shows that trialkyltin chloride formation is largely supressed by a catalyst composition containing the same trihydrocarbyl catalyst in an analogous system.

The present catalyst composition is used in quite modest concentrations, of the order of 0.01 to 0.2 mole stannic chloride and $R_3E$ mixture per mole of dialkyltin dichloride. However, these properties are not critical and may be varied. The yields of trialkyltin chloride are improved and the reaction time is reduced compared to prior art processes. Most importantly, the formation of undesirable tetraalkyltin by-product is suppressed. The last result is particularly important in the preparation of trimethyltin chloride and triethyltin chloride, for instance, where the absence of the volatile, flammable, and generally hazardous tetraalkyltin by-product greatly facilitates the design of equipment and procedures for manufacture with minimal release of organotin to the work area and the external environment. The absence of tetraalkyltin by-product is also of value in the preparation of higher molecular weight trialkyltin chlorides, for example tributyltin chloride and trihexyltin chloride, since with increasing molecular weight the separation of trialkyltin chloride from tetraalkyltin becomes progressively more difficult with these products.

Each of the stannic chloride and $R_3E$ ingredients of the present catalyst as well as each of the polyvalent metal and polar liquid reactants is essential to the successful working of the process of this invention; absent any one of these, the high yield and rapid production of trialkyltin chloride substantially free of objectionable tetraalkyltin are not realized. In the absence, for example, of the stannic chloride and $R_3E$ catalyst, the reaction of a dialkyltin dichloride such as dimethyltin dichloride with iron metal and water, for instance, gives a greatly reduced yield of trimethyltin chloride mixed with considerable quantities of tetramethyltin, while in the presence of the catalyst without the polar liquid, dimethyltin dichloride can be heated with polyvalent metal without forming any appreciable amount of trimethyltin chloride.

DESCRIPTION OF PREFERRED EMBODIMENTS

The trialkyltin chloride prepared by the process of this invention, and the dialkyltin dichloride starting material can comprise straight chain or branched alkyl groups having from 1 to 6 carbon atoms including cyclopentyl and cyclohexyl and can be the same or different. In the dialkyltin dichloride starting material, the primary straight chain alkyl groups, i.e. methyl, ethyl, n-propyl, n-butyl, n-amyl, and n-hexyl, which also can be the same or different, make up a preferred group in which methyl and ethyl are particularly preferred. Accordingly, the preferred trialkyltin chlorides prepared by the process of this invention include trimethyltin chloride, triethyltin chloride, tri-n-propyltin chloride, tri-n-butyltin chloride, tri-n-amyltin chloride and tri-n-hexyltin chloride the first two of which are particularly preferred. Tri-cyclopentyltin chloride and tri-cyclohexyltin chloride, for instance, can also be prepared by a process in accordance with this invention, starting from dicyclopentyltin dichloride and dicyclohexyltin dichloride respectively.

Mixed trialkyltin chlorides are also obtainable by the use of more than one dialkyltin dichloride starting material by the process of this invention. Dimethyl hexyltin chloride and methyl-di-n-hexyltin chloride, for example, can be prepared and subsequently separated from one another if desired by means known in the art.

The polyvalent metal reagent in the process of this invention has an electrode potential in the range from about −0.14 volt to −1.7 volt and can be any one or more of aluminum, cadmium, chromium, cobalt, iron, nickel, tin, and zinc, for instance. Iron and tin are preferred. The quantity of metal reagent used in the process of this invention is preferably at least one-third gram-atom per mole of dialkyltin dichloride. An excess of metal reagent can be charged if desired, and the unused portion recycled for further use. The particle size of the metal reagent is not critical and is chosen with a view to convenient loading, unloading, and agitation of the reaction mixture.

The polar liquid reagent in the process of this invention can be acetonitrile, methanol, water, other alcohols and generally any unreactive polar liquid reagent. Water, of course, is preferred for reasons of convenience and cost. The quantity of polar liquid reagent employed is preferably one mole per mole of dialkyltin dichloride, but may be used in excess without adverse effect. When less than one mole of polar liquid per mole of dialkyltin dichloride is present, however, the extent of conversion of the latter is limited by the amount of polar liquid present. The polar liquid is selected from among liquids which are free of groups that react with the polyvalent metal reagent such as halogen or nitro groups.

In the catalyst consisting essentially of a mixture of stannic chloride and a nitrogen or phosphorus compound $R_3E$, R can be any of the above recited alkyl groups as well as other hydrocarbon groups, such as n-heptyl, n-octyl, 2-ethylhexyl, isooctyl, phenyl, and each of the isomeric tolyls, xylyls, and ethylphenyls, for instance. Particularly suitable catalyst components $R_3E$ include triethylamine, tri-n-butylamine, tri-n-butylphosphine, N,N-diethylaniline "and triphenylphosphine" being preferred in the present system.

The process of this invention can be carried out over a convenient range of reaction temperatures, suitably at the atmospheric pressure refluxing temperature of the reaction mixture. Superatmospheric pressure is not necessary to the successful operation of the process but can be applied if desired as an expedient to assure absolute containment of the reaction mixture and products in the vessel and avoid any possible escape of potentially irritating or objectionable material therefrom.

Accordingly, suitable operating temperatures for the process of this invention range from about 90° to about 200° C.

The use of a solvent is not required to the successful operation of the process of this invention, but can be practiced, if desired. An excess of the polar liquid reactant can be used as solvent, as can ethers, esters, ketones, hydrocarbons, and the like.

Conventional techniques such as crystallization, solvent extraction, and distillation can be used to recover the trialkyltin chloride product prepared according to this invention.

EXAMPLE I

A catalyst composition was prepared by the exothermic reaction of one mole of triphenylphosphine with one mole of stannic chloride. A 10 g portion of this catalyst was mixed with 132 g dimethyltin dichloride, 33.5 g iron powder, and 10.8 g water, and the mixture warmed to 140° C. during 50 minutes in a distillation apparatus. Distillation of the liquid mixture was started, and carried on while 76.7 g material boiling in the range of 106° to 155° C. passed over as a first distillate. To the residue 100 ml water was added, and the distillation was continued to yield 10.4 g material boiling in the range 95° to 100° C. as a second distillate.

The two distillates were analyzed by proton magnetic resonance spectroscopy. The first distillate contained 85.7% trimethyltin chloride, 5.7% dimethyltin dichloride, 8.6% water, and no tetramethyltin. The second distillate contained 45.9% trimethyltin chloride, 54.1% water, and no tetramethyltin. The combined amount of trimethyltin chloride in the two distillates thus amounts to a 91.4% yield based on the amount of dimethyltin dichloride consumed.

EXAMPLE II

A mixture of 10 g triphenylphosphine-stannic chloride catalyst, 132 g dimethyltin dichloride, 33.5 g iron powder, and 21.6 g water was stirred and heated in a distillation apparatus. The temperature of the mixture reached 144° C. and then fell as distillation began, remaining in the 115°–120° C. range while the distillation continued. Wat totaling 100 ml was added at intervals during the distillation.

The distillate, boiling from 101° to 107° C. weighed 104.2 g and consisted only of trimethyltin chloride 69.7% and water 30.3% by weight, tetramethyltin and dimethyltin dichloride being absent. The trimethyltin chloride produced represented a 91% of theoretical yield.

EXAMPLE III

A mixture of 10 g triphenylphosphine-stannic chloride catalyst, 132 g dimethyltin dichloride, 33.5 g iron powder, 5.4 g water, and 50 g toluene was heated under reflux for 3½ hours. During the last hour the temperature reached 115°-118° C. The product was diluted with additional 50 ml toluene and filtered.

Analysis of the filtrate showed the presence only of toluene, trimethyltin chloride (49.9% on solvent free basis), and dimethyltin dichloride starting material (B 50.1% on solvent free basis).

This result shows the operation of the process of this invention in presence of an organic solvent to give a fair yield of trimethyltin chloride without tetramethyltin containment. The persistence of unconverted starting material is the result of an insufficient quantity of water present.

EXAMPLE IV

A mixture of 132 g of dimethyltin dichloride, 33.5 g of iron powder, and 24.2 ml of methanol was heated under reflux with stirring, to a maximum temperature of 111° C. after 1 hour. When distillation proceeded, the internal temperature dropped as low as 99° C.

Distillation was continued until the contents of the vessel became too thick to stir. A total of 16.4 g distillate boiling in the range 71° to 84° C. was collected. Analysis showed the presence of much methanol, tetramethyltin (60.7% by weight on solvent free basis), and trimethyltin chloride (39.3% solvent free basis).

EXAMPLE V

A mixture of 66 g dimethyltin dichloride and 16.7 g iron powder was stirred and heated under reflux at 138°-140° C. for 2½ hours. There was no visible sign of reaction and analysis showed dimethyltin dichloride as the only tin compound present.

EXAMPLE VI

A mixture of 132 g dimethyltin dichloride, 33.5 g iron powder, and 10.8 g water was heated with stirring under reflux for 3 hours and the product isolated by simple distillation, (cut 1, 64 g) followed by azeotropic distillation with water (cut 2, 26 g). The distillate from cut 1 separated into two phases. One phase (11.7 g) consisted of 60% trimethyltin chloride and 40% tetramethyltin; the other phase (52.1 g) consisted of 80% trimethyltin chloride and 20% water.

The results of the foregoing examples clearly demonstrate the beneficial unexpected results by the process of this invention. In the absence of catalyst and polar liquid, there is zero conversion of dimethyltin dichloride. With a polar liquid present and no catalyst, there is some conversion of dimethyltin dichloride but the product contains a considerable amount of undesirable tetramethyltin. By the process of the present invention there is a high conversion of dimethyltin dichloride to trimethyltin chloride sans tetramethyltin.

The present invention is not limited to the specific examples and other embodiments disclosed herein and includes such changes and modifications as may be apparent to one skilled in the art upon reading the following claims.

The embodiments of the invention in which an exclusive property or privelege is claimed are defined as follows:

1. In a process for the preparation of a trialkyltin chloride in which the alkyl groups contain from one to six carbon atoms, by heating a mixture containing a dialkyltin dichloride, a polyvalent metal having an electrode potential in the range from −0.14 volt to −1.7 volt, and a polar liquid, the improvement comprising the presence of a catalytic amount of a catalyst consisting essentially of stannic chloride and a compound having the formula $R_3E$ in which each R is a hydrocarbon group having 1 to 8 carbon atoms and E is a member of the group consisting of nitrogen and phosphorus, in which the molar proportions of stannic chloride to compound $R_3E$ range from about 1:4 to about 1:1.

2. A process according to claim 1 in which alkyl is methyl.

3. A process according to claim 1 in which alkyl is n-butyl.

4. A process according to claim 1 in which alkyl is n-hexyl.

5. A process according to claim 1 in which the polyvalent metal is iron.

6. A process according to claim 1 in which the polyvalent metal is tin.

7. A process according to claim 1 in which R is phenyl.

8. A process according to claim 1 in which E is phosphorus.

9. A process according to claim 1 in which the molar properties of stannic chloride to $R_3E$ is from 0.9 to 1:1.

10. A process according to claim 9 wherein R is phenyl and E is phosphorus.

* * * * *